United States Patent
Yeung et al.

(10) Patent No.: US 10,184,896 B2
(45) Date of Patent: Jan. 22, 2019

(54) SYSTEM, APPARATUS AND METHOD FOR VIEWING A GEMSTONE

(71) Applicants: GOLDWAY TECHNOLOGY LIMITED, Hong Kong (CN); PSP SECURITY COMPANY LIMITED, Hong Kong (CN)

(72) Inventors: Wai Keung Yeung, Hong Kong (CN); Wing Chiu Liu, Hong Kong (CN)

(73) Assignee: GOLDWAY TECHNOLOGY LIMITED, Hong Kong (HK)

( * ) Notice: Subject to any disclaimer, the term of this patent is extended or adjusted under 35 U.S.C. 154(b) by 0 days.

(21) Appl. No.: 15/517,516

(22) PCT Filed: Oct. 7, 2015

(86) PCT No.: PCT/CN2015/091427
§ 371 (c)(1),
(2) Date: Apr. 7, 2017

(87) PCT Pub. No.: WO2016/054996
PCT Pub. Date: Apr. 14, 2016

(65) Prior Publication Data
US 2017/0307537 A1   Oct. 26, 2017

(30) Foreign Application Priority Data
Oct. 7, 2014 (HK) .................................. 14109995

(51) Int. Cl.
*G01N 21/00* (2006.01)
*G01N 21/87* (2006.01)
*G02B 27/02* (2006.01)

(52) U.S. Cl.
CPC ........... *G01N 21/87* (2013.01); *G02B 27/022* (2013.01); *G01N 2201/062* (2013.01)

(58) Field of Classification Search
CPC ........ G01N 21/87; G01N 21/88; G01N 21/64; G01N 21/65; G01N 33/381
See application file for complete search history.

(56) References Cited

U.S. PATENT DOCUMENTS

| 2007/0036921 A1 | 2/2007 | Twitchen | |
|---|---|---|---|
| 2008/0055582 A1* | 3/2008 | Lapa ..................... | G01N 21/87 356/30 |
| 2011/0228063 A1* | 9/2011 | Smith .................... | G01N 21/87 348/61 |

FOREIGN PATENT DOCUMENTS

| CN | 101762586 A | 6/2010 |
|---|---|---|
| CN | 103635793 A | 3/2014 |

(Continued)

OTHER PUBLICATIONS

International Search Report & Written Opinion of PCT/CN2015/091427.
Search Report by UKIPO for Priority Application No. 14109995.0.

*Primary Examiner* — Abdullahi Nur
(74) *Attorney, Agent, or Firm* — Joseph G. Chu; JCIP (57) ABSTRACT

A system (1) for viewing a gemstone, the system (1) including a first light source (2) configured for selectably illuminating at least one of a plurality of features of the gemstone; an optical magnifying unit (10) configured for providing a magnified view of the plurality of the features of the gemstone in which at least one of the plurality of features of the gemstone is selectably illuminated by the first light source (2); and a viewing display unit (11) configured for displaying a representation of the magnified view.

23 Claims, 6 Drawing Sheets

(56) References Cited

FOREIGN PATENT DOCUMENTS

| EP | 1795888 A1 | 6/2007 |
|----|------------|--------|
| JP | 2011161206 A | 8/2011 |
| WO | 2013013685 A1 | 1/2013 |
| WO | 2014171600 A1 | 10/2014 |

* cited by examiner

SYSTEM, APPARATUS AND METHOD FOR VIEWING A GEMSTONE

TECHNICAL FIELD

The present invention relates to the field of the viewing gemstones, and more particularly methods, device and systems therefore.

BACKGROUND OF THE INVENTION

Throughout history, craftsmen have endeavored to produce appealing illumination effects from gemstones, which has historically been by cutting a gemstone such that light may be captured and redirected to the eye of an observer.

A variety of cuts are used on a gemstone such that a plurality of facets are formed on the gemstone. The facets in the crown capture light, whereas facets in the pavilion of the gemstone reflects light by total internal reflection. It is the capture and redirection of light which gives the appearance of a gemstone being illuminated, with the effects of illumination being those including the parameters of brilliance, fire and scintillation.

Cut precision of gemstones affects the performance of gemstones such as diamonds, and a better defined pattern can provide, for example, sharper on-off scintillation and more primary colors in dispersion. Precision cutting is known to maximise the return of all available light applied to a diamond, which is a result of all of the facets being in precise alignment with each other.

When a diamond is cut with such precision that its facet reflections overlap with each other, this produces uniform, kaleidoscopic patterns when observed typically from the crown or the pavilion of a diamond.

In order to achieve such precision, increased stone wastage is required, in addition to increased working times and costs. Only a small portion of the world's diamonds are cut with such precision so as to provide crisp, uniform patterns.

A predominant example of diamonds cut to such precision termed in the art "Hearts and Arrows" precision cut, which are precision cut variations of the traditional 57 faceted round brilliant cut. Such a cut is termed "Hearts and Arrows" as when viewed upside-down (the "pavilion") the overlapping reflections create a pattern of eight symmetrical hearts in the pavilion, and when viewed upside-right (the "crown") eight radiating arrows in the crown may be seen. Devices for viewing such diamonds and light reflection phenomena, light from above is coded white and light from the sides is coded, for example blue, or red or green.

Other diamond cuts which may provide such phenomena is the Princess cut, which typically has 24-48 facets on the pavilion and 17-29 cut on the crown, and variations of pattern result. Such a cut provides overlapping reflections which create a series of white and red V's in the pavilion of the diamond, and primary "X" pattern running through the crown of the diamonds.

The viewing of such light patterns on diamonds is used to determine the quality of the cut, with typically greater precision cutting providing more uniform or consistent facet reflection patterns with respect to other facet reflection patterns.

Viewer devices for viewing patterns in gemstones, such as "Hearts and Arrows" quality diamonds, are cylindrical devices having a magnifying lens at one end, and a locator for a diamond, and illumination is from ambient light. To view the Arrows pattern, the diamond is inserted such that the crown is faced towards the magnifying lens, and to view the Hearts pattern the pavilion of the diamond is faced towards the magnifying lens.

SUMMARY OF THE INVENTION

The present invention seeks to alleviate at least one deficiency associated with the prior art.

The present invention may involve several broad forms. Embodiments of the present invention may include one or any combination of the different broad forms herein described.

In a first broad form, the present invention provides a method of selectably viewing at least one light-activatable feature of a plurality of light-activatable features of a gemstone, wherein at least one portion of a plurality of portions of the gemstone corresponding to the at least one light-activatable feature is selectably illuminated by a first light source so as to selectably activate said at least one light-activatable feature and to provide said selectable viewing thereof.

Preferably, the plurality of light-activatable features of the gemstone may form an optically-viewable pattern.

Preferably, the optically-viewable pattern may include at least one of a plurality of hearts, a plurality of arrows, a star and a plurality of triangles.

Preferably, the plurality of portions of the gemstone may include facets of the gemstone.

Preferably, the first light source may include an infrared light source.

Preferably, the first light source may include an LED light source.

Preferably, the first light source may include a plurality of LEDs.

Preferably, the at least one light-activatable feature of the gemstone may be selectably activated discretely or variably.

Preferably, a light separator may be configured for directing light emitted from the first light source to selectably illuminate the at least one portion of the gemstone corresponding to the light-activatable feature so as to activate the at least one light-activatable feature.

Preferably, the present invention may include a second light source configured for illuminating the gemstone so as to produce a viewable coloured background feature of the gemstone.

Preferably, the second light source may include at least one of a red coloured light source and a blue coloured light source.

Preferably, the second light source may include a plurality of coloured light LEDs.

Preferably, the present invention may include a diffusor configured for diffusing light emitted from the second light source.

Preferably, the present invention may include a third light source configured for illuminating the gemstone so as to produce a viewable sparkling feature of the gemstone.

Preferably, the third light source may include a plurality of white light LEDs.

Preferably the system further comprising a rotation assembly for rotation of one of the light sources and the gemstone relative to each other about the viewing axis of the optical acquisition device, such that light from said of the light sources is applied towards the gemstone from one facet to an adjacent facet upon said rotation. The rotation assembly may provide rotation of the third light source and the gemstone relative to each other, and wherein light applied towards the gemstone is applied with a constant intensity from a facet of the gemstone to an adjacent facet throughout rotation so as to provide said viewable sparkling feature of the gemstone.

Preferably, the present invention may include an optical viewing unit for viewing an optical representation of the light-activatable feature of the gemstone.

Preferably, the optical viewing unit may include at least one of a television display, a computer monitor, and a display screen of a smartphone or portable communication device.

Preferably, the light-activatable feature of the gemstone may be communicated to the viewing display unit for viewing via a wireless communication link.

Preferably, the present invention may include a magnifying unit for optically magnifying the representation of the light-activatable feature of the gemstone.

Preferably, the magnifying unit may be configured to provide a first magnified view comprising a relatively lower magnification of the representation of the light-activatable feature of the gemstone and a second magnified view comprising a relatively higher magnification of a representation of another feature of the gemstone, wherein said another feature of the gemstone includes a marking feature.

Preferably, the optical viewing unit may be configured to display the first and second magnified views interchangeably, or, concurrently whereby the first magnified view is displayed inset within the second magnified view.

Preferably, the present invention may include a controller for controlling at least one of the first light source, the second light source, and the third light source to illuminate the gemstone in accordance with a predetermined lighting sequence.

Preferably, the predetermined lighting sequence may be synchronised to music.

In a second broad form, the present invention provides a system for selectably viewing at least one light-activatable feature of a plurality of light-activatable features of a gemstone, the system including:

a first light source configured for selectably illuminating at least one portion of a plurality of portions of the gemstone corresponding to the at least one light-activatable feature of the gemstone wherein the at least one light-activatable feature of the gemstone is activated in response to selectable illumination of the at least one portion of the gemstone; and an optical acquisition device configured for optically acquiring an optically-viewable representation of the at least one light-activated feature which is activated in response to selectable illumination of the at least one corresponding portion of the gemstone.

Preferably, the plurality of light-activatable features of the gemstone may form an optically-viewable pattern.

Preferably, the optically-viewable pattern may include at least one of a plurality of hearts, a plurality of arrows, a star and a plurality of triangles.

Preferably, the plurality of portions of the gemstone may include facets of the gemstone.

Preferably, the first light source may include an infrared light source.

Preferably, the first light source may include an LED light source.

Preferably, the first light source may include a plurality of LEDs.

Preferably, the at least one light-activatable feature of the gemstone may be selectably activated discretely or variably.

Preferably, the present invention may include a light separator configured for directing light emitted from the first light source to selectably illuminate the at least one portion of the gemstone corresponding to the light-activatable feature so as to activate the at least one light-activatable feature.

Preferably, the present invention may include a second light source configured for illuminating the gemstone so as to produce a viewable coloured background feature of the gemstone.

Preferably, the second light source may include at least one of a red coloured light source and a blue coloured light source.

Preferably, the second light source may include a plurality of coloured light LEDs.

Preferably, the present invention may include a diffusor configured for diffusing light emitted from the second light source.

Preferably, the present invention may include a third light source configured for illuminating the gemstone so as to produce a viewable sparkling feature of the gemstone.

Preferably, the third light source may include a plurality of white light LEDs.

Preferably, the present invention may include an optical viewing unit for viewing the optical representation of the light-activatable feature of the gemstone optically acquired by the optical acquisition device.

Preferably, the optical viewing unit may include at least one of a television display, a computer monitor, and a display screen of a smartphone or portable communication device.

Preferably, the present invention may include a wireless communication link via which the optical representation of the light-activatable feature of the gemstone acquired by the optical acquisition device may be communicated to the viewing display unit from the optical acquisition device for viewing thereon.

Preferably, the present invention may include a magnifying unit for optically magnifying the representation of the light-activatable feature of the gemstone.

Preferably, the magnifying unit may be configured to provide a first magnified view comprising a relatively lower magnification of the representation of the light-activatable feature of the gemstone and a second magnified view comprising a relatively higher magnification of a representation of another feature of the gemstone, wherein said another feature of the gemstone includes a marking feature.

Preferably, the optical viewing unit may be configured to display the first and second magnified views interchangeably, or, concurrently whereby the first magnified view is displayed inset within the second magnified view.

Preferably, the present invention may include a controller for controlling at least one of the first light source, the second light source, and the third light source to illuminate the gemstone in accordance with a predetermined lighting sequence.

Preferably, the present invention may include a device for synchronising the predetermined lighting sequence to music.

Preferably, the system may be configured as a portable unit.

Preferably, the first light source may be configured to illuminate the at least one portion of the plurality of portions of the gemstone at an angle approximately in a range of about 75 to 83 degrees.

Preferably, the present invention may include a PCB having an inner and an outer ring portion, wherein the first light source is mounted on the inner ring portion and the second and third light sources may be mounted on the outer ring portion.

Preferably, the present invention may further provide for the viewing of an invisible marking on a facet of a gemstone, whereby the marking is provided by one or more protrusions formed on an outer surface of a polished facet of the gemstone, wherein the polished facet of the solid state material has an average surface roughness of less than 50 nm.

Preferably, such an invisible marking may be formed from a plurality of protrusions formed which may be nanometer sized so as so provide an information mark invisible to the naked eye due to Rayleigh Criterion in optical limit.

Preferably, the one or more protrusions may be arranged in a periodic array viewable by specified lighting conditions and by a camera equipped microscope in the visible and invisible light range. Also preferably, the one or more protrusions may be adjoined to an adjacent protrusion, so as to form a continuous nano-protrusion marking arranged in a periodic array viewable by specified lighting conditions and by a camera equipped microscope in the visible and invisible light range.

Preferably, the system may further include a further light source for illuminating said marking for detection and viewing of the marking by optical magnifying unit, wherein upon application of specific lighting conditions or the optical viewing conditions the optical viewing unit may view the marking in the visible and invisible light range.

Preferably, such a marking may be formed from the steps including (i) applying focused inert gas ion beam local irradiation towards an outer surface of a polished facet of the gemstone in a way of protruding top surface material; wherein irradiated focused inert gas ions from said focused inert gas ion beam penetrate the outer surface of said polished facet of said gemstone; and irradiated focused inert gas ions cause expansive strain within the solid state crystal lattice of the gemstone below said outer surface at a pressure so as to induce expansion of solid state crystal lattice, and form a protrusion on the outer surface of the polished facet of the gemstone. Preferably, the focused inert gas ion beam has a beam energy in the range of from 5 keV to 50 keV and probe current 1 fA to 200 pA. The solid state crystal lattice may be in a form of single crystalline, poly-crystalline, or amorphous form.

In another broad form the present invention provides a system for viewing a further identifiable mark on an article on a portion of a polished facet of a surface of a gemstone, and further comprising:
  a light source for incident light having one or more predetermined wavelengths at a predetermined angle of incidence to the identifiable mark; and
  an optical viewing device for viewing said identifiable mark at said requisite viewing angle by way of an optical viewing device such that a local maxima is detected,
  wherein the identifiable mark comprises a nano-structure formed by a two-dimensional or a three-dimensional lattice of a plurality of discrete nanometer sized recessed or protruded entities, wherein said entities are arranged within a predefined region of said polished facet in a predetermined arrangement in relation to each other, and such that an outer interface surface between the facet of the article and air is formed and an inner interface surface between the facet of the article and air is formed;
  wherein said predetermined arrangement of said entities is a non-uniform and non-periodic arrangement, and wherein said entities are sized and shaped so as to cause optical scattering upon reflection of incident light, and the distance from the inner interface surface to the outer interface surface is greater than the amplitude of the non-marked portion of said polished facet;
  such that upon reflection of incident light having one or more predetermined wavelengths by said lattice at a predetermined angle of incidence to said lattice, interference due to scattering of light from said lattice is induced, such that reflected light has a variation in intensity providing one or more local maxima of one or more wavelengths; and
  said mark is identifiable by way of the optical viewing device inclined at a requisite viewing angle such that a local maxima is detected.

In a further broad form, the present invention provides a system for viewing a further non-optically identifiable marking on a polished facet of a gemstone, wherein the non-optically detectable identifiable mark may be non-optically detectable in the visible light spectrum is viewable in the ultra-violet (UV) spectrum, and the system includes an ultra-violet light source for illuminating said marking.

Preferably, the system may further include a Differential Interference Contrast (DIC) microscope or Scanning Electron Microscopy (SEM) for viewing of said further marking. Also preferably, such a marking may be formed by a method including the steps of:
  (i) forming a plurality of recesses within a predetermined region of a photoresist applied to an outer surface of an article formed from a solid state material, wherein said plurality of recesses is formed by two-photon absorption lithography and wherein said one or more recesses extend at least partially through the photoresist and from an outer surface of the photoresist and towards said outer surface of the article formed from a solid state material; and
  (ii) applying an etching process such that at least a portion of the outer surface of said article is exposed and etched so as to form a plurality of etched portions extending into said article from the outer surface of the article and corresponding to said plurality of recesses;
  wherein said predetermined region of said photoresist defines an identifiable mark to be applied to the outer surface of said article; wherein said plurality of etched portions forms the non-optically identifiable mark on the outer surface of said article; and wherein the maximum width of the etched portions is less than 200 nm such that the identifiable mark is non-optically detectable in the visible light spectrum.

In another broad form, the present invention provides a device for selectably viewing at least one light-activatable feature of a plurality of light-activatable features of a gemstone, wherein the device includes the system of the second broad form of the present invention.

In a further broad form, the present invention provides a method of verifying the identity of a gemstone, said method comprising:
  selectably illuminating at least one portion of a plurality of portions of a gemstone corresponding to the at least one light-activatable feature of the gemstone wherein the at least one light-activatable feature of the gemstone is activated in response to selectable illumination of the at least one portion of the gemstone;
  acquiring an optically viewable representation of the at least one light-activated feature which is activated in response to selectable illumination of the at least one corresponding portion of the gemstone; and comparing said optically viewable representation with a known optical representations, whereby said known optical representations are indicative of a particular gemstone.

Preferably, the plurality of light-activatable features of the gemstone form an optically-viewable pattern, and wherein facet reflections which overlap with each other form said optically viewable pattern.

In yet another broad form, the present invention provides a system for verifying the identity of a gemstone, said system comprising:
- a first light source configured for selectably illuminating at least one portion of a plurality of portions of the gemstone corresponding to the at least one light-activatable feature of the gemstone wherein the at least one light-activatable feature of the gemstone is activated in response to selectable illumination of the at least one portion of the gemstone;
- an optical acquisition device configured for optically acquiring an optically viewable representation of the at least one light-activated feature which is activated in response to selectable illumination of the at least one corresponding portion of the gemstone; and
- a processor for comparing said optically viewable representation of the at least one light-activated feature with known optical representations, whereby said known optical representations are indicative of a particular gemstone.

Preferably the plurality of light-activatable features of the gemstone may form an optically-viewable pattern, and wherein facet reflections which overlap with each other form said optically viewable pattern.

In yet another broad form, the present invention provides a system for assessing the precision of a plurality of cuts of a gemstone, said system comprising:
- a first light source configured for selectably illuminating at least one portion of a plurality of portions of the gemstone corresponding to the at least one light-activatable feature of the gemstone wherein the at least one light-activatable feature of the gemstone is activated in response to selectable illumination of the at least one portion of the gemstone;
- an optical acquisition device configured for optically acquiring an optically viewable representation of the at least one light-activated feature which is activated in response to selectable illumination of the at least one corresponding portion of the gemstone; and
- a processor for comparing said optically viewable representation of the at least one light-activated feature known optical representations, whereby said known optical representations are indicative of a cut parameter of the facets of the gemstone.

BRIEF DESCRIPTION OF THE DRAWINGS

The present invention will become more fully understood from the following detailed description of a preferred but non-limiting embodiment thereof, described in connection with the accompanying drawings, wherein.

DETAILED DESCRIPTION OF THE PREFERRED EMBODIMENTS

Cut Precision of gemstones affects the performance of gemstones such as diamonds, and a better defined pattern can provide, for example, sharper on-off scintillation and more primary colors in dispersion. Precision cutting is known to maximize the return of all available light applied to a diamond, which is a result of all of the facets being in precise alignment with each other.

When a diamond is cut with such precision that its facet reflections overlap with each other, this produces uniform, kaleidoscopic patterns when observed typically from the crown or the pavilion of a diamond.

In order to achieve such precision, increased stone wastage is required, in addition to increased working times and costs. Only a tiny fraction of the world's diamonds are cut to such precision that they will show crisp, uniform patterns.

A preferred embodiment of the present invention will now be described with reference to the drawings FIGS. 1 to 7 which is configured for selectably viewing at least one light-activatable feature of a plurality of light-activatable features of a gemstone which are activated in response to selectable illumination of portions of the gemstone corresponding to the light-activatable features of the gemstone.

Figure 2:
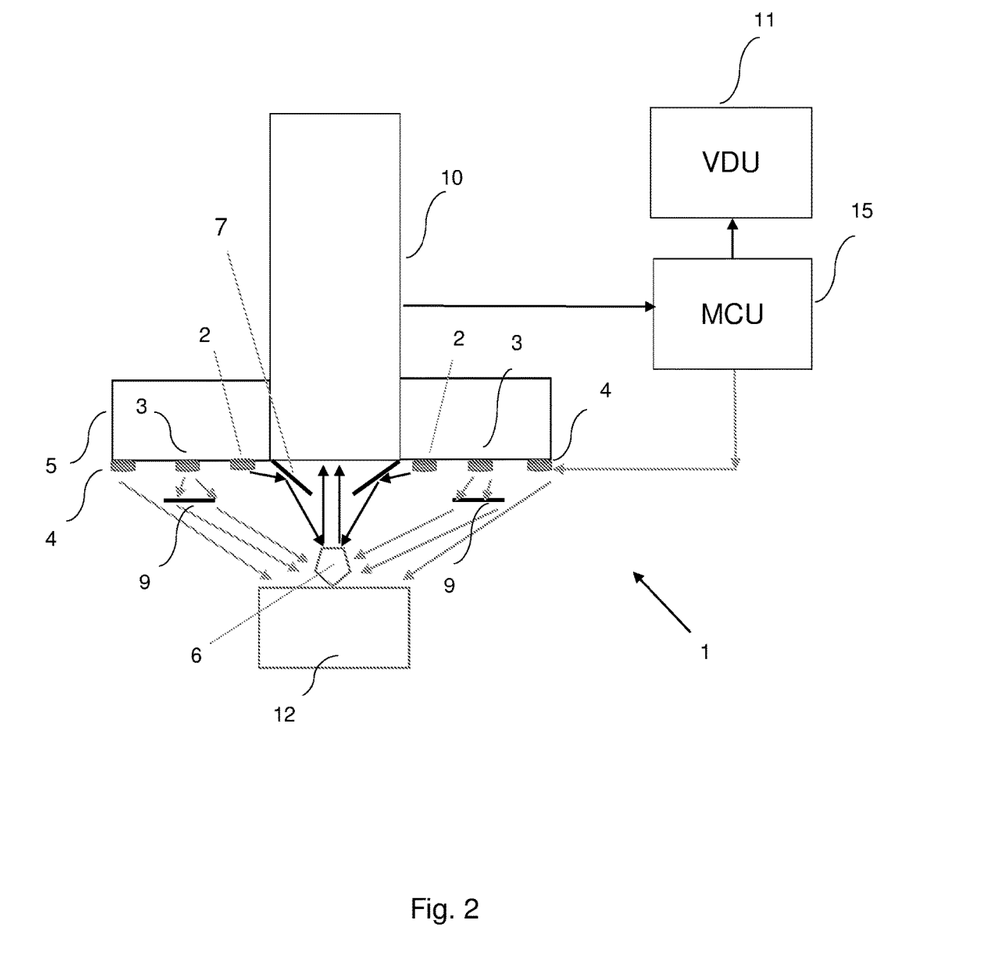
FIG. 2 shows a side view of a functional block diagram of a first embodiment system for viewing a gemstone.

The system (1) includes a first (2), a second (3) and a third (4) set of LED light sources of varying light emission characteristics which are operably mounted to a PCB (5) for illuminating the gemstone (6). The system also includes a conical reflector (7), an LED separator (8), a diffusor (9), an optical magnifying unit (10) for magnifying the gemstone under illumination, and, a viewing display unit (11) for viewing one or more magnified images of the illuminated gemstone under varying magnification.

Embodiments of the present invention also include a fixture assembly (12) for mounting the gemstone (6) in a viewing position proximate to the viewing system (1). The fixture assembly (12) includes an elevator which can move the diamond (6) up and down (linear motion in Z direction) by turning a wheel to enable focusing on the diamond. Its resolution is high enough for fine focusing of a mark or feature on the gemstone.

A coaxial rotary support base is also provided—for instance, a turntable, having a rotary axis well aligned to the optical axis so that, once a mark or feature on the diamond is well located and focused, the user can change the orientation only without losing the mark or feature in the marking view by rotating this support base (i.e. rotation motion along the Z-axis).

An iron plate is fixed onto the rotary support base. It works together with a magnet to generate an attractive force to stabilize the posture of ring holder. A plastic bearing (socket of the ball-and-socket joint) is provided whereby its upper surface allows the ring holder to rotate on it smoothly when applying force but at the same time has high enough friction to hold the posture of ring holder when no force is applied on it. Its lower surface also allows the ring holder to slide smoothly along the iron plate horizontally. A standard ring holder (ball of the ball-and-socket joint) is also provided whereby the material and cloth inside the holder forms a slot for holding a ring or earring in upright orientation. It allows linear motion in X and Y directions, and rotation motion along X and Y axes. A magnet is further provided in the ring holder whereby it works together with the iron plate to stabilize the posture of ring holder.

A naked gemstone holding adaptor is yet further provided which can be installed directly onto the ring holder for holding naked gemstones either in upright orientation or in upside-down orientation. Yet further, a necklace holding adaptor is also provided whereby it can be installed directly onto the ring holder for holding necklace of different designs and styles. The surface of the adaptor has six troughs and a rubber coating for providing enough friction for holding the necklace in position.

Yet further, a bracelet holder is provided which allows a bracelet to be held and viewed under the optics. Yet further, a girdle viewing holder is provided whereby this holder holds rings and earrings with bending angle of 90 degree which allows the girdle of a gemstone be viewed by the optics. In summary, the fixtures of the fixture assembly assists the setting of clear viewing of a mark or feature on a gemstone to be viewed by providing 6 degrees of freedom for the adjustment of the orientation, focus, reflection of light source and X-Y positioning of gemstone under the optics.

Figure 1A:
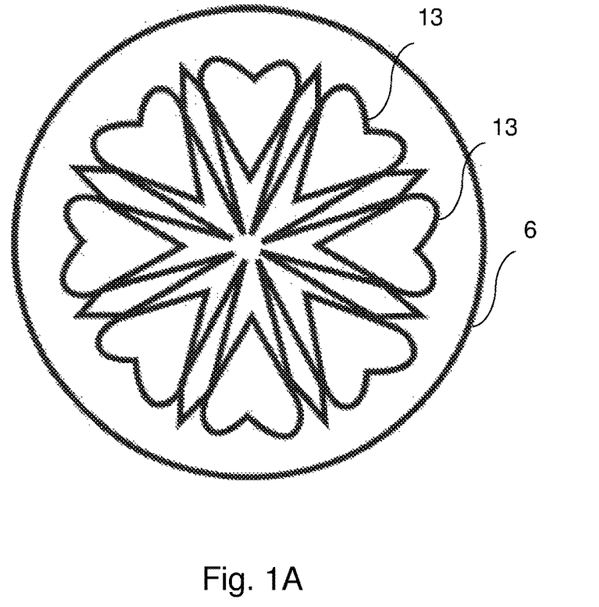
FIG. 1A shows an optically-viewable pattern of "hearts" disposed on a "hearts and arrows" cut diamond.
Figure 1B:
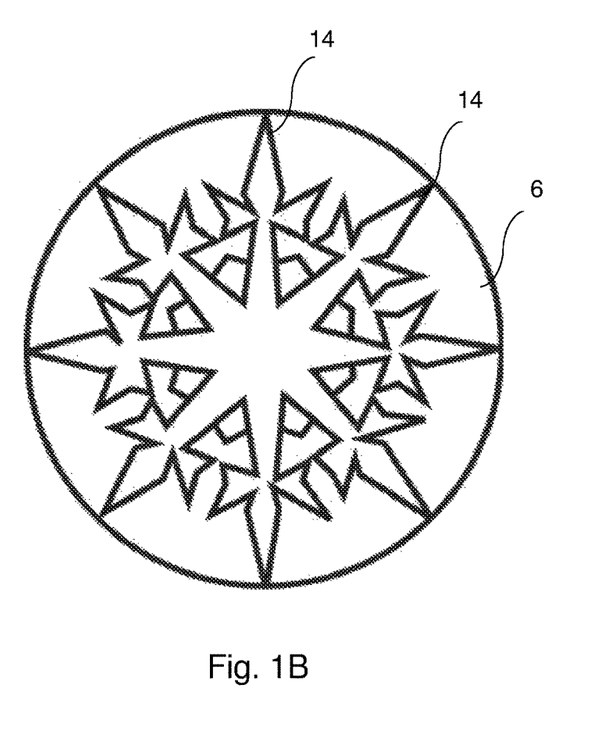
FIG. 1B shows an optically-viewable pattern of "arrows" disposed on a "hearts and arrows" cut diamond.
Figure 4:
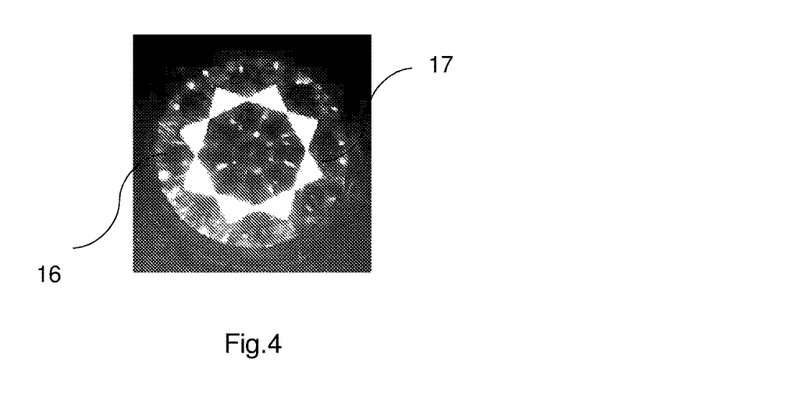
FIG. 4 shows an exemplary optically viewable pattern of a gemstone in the form of a star-shaped pattern.

Embodiments of the present invention are described in use for selectably viewing a plurality of light-activatable features of a gemstone such as a diamond having a plurality of facets cut into it. The plurality of light-activatable features may collectively form any number of different optically-viewable patterns including but not limited to a "star"-shaped pattern (i.e. comprising 8 triangle shapes which form such a "star" pattern (17)) as depicted in FIG. 4, a plurality of 8 arrows pattern as shown in FIG. 1A, and, a plurality of 8 hearts pattern as depicted in FIG. 1B. It will be appreciated that the system is configurable for viewing other types of gemstones and any different types of cuts and configurations of such gemstones.

The PCB (5) comprises of two concentric rings—an inner ring and an outer ring. The first light source includes 8 LEDs (2) which are operably mounted on the inner ring of the PCB. Light emitted from each of the 8 LEDs (2) are configured to selectably illuminate corresponding facets of the gemstone in such a way that light-activatable features corresponding to the selectably illuminated portions of the gemstone are viewable. As the system is able to be utilised for viewing light-activatable features of a variety of different gemstones having different types of cuts, the angle(s)/direction(s) of light emissions from the first light source may be manually and/or automatically reconfigured in order to suitably direct the light emissions from the first light source towards facets of the gemstone in such a manner necessary to selectably activate the corresponding light-activatable features resulting from illumination of the facets.

Figure 5:
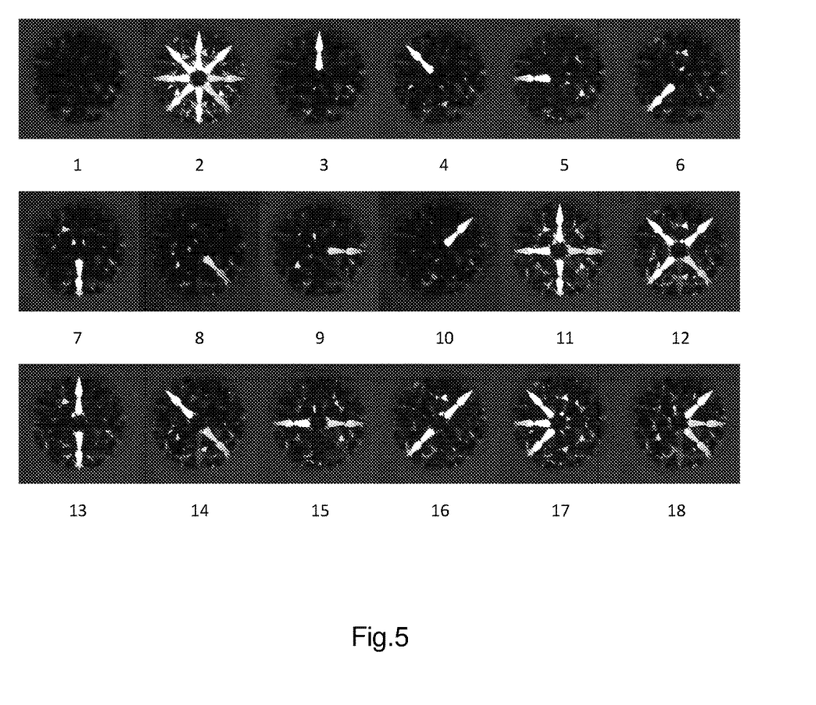
FIG. 5 shows an exemplary sequence of light-activatable features of a gemstone wherein the light-activatable features form an optically-viewable pattern including representations of "arrows" and part "arrows"

FIG. 5 shows an exemplary sequence (depicted by frames 1 to 18) of light-activatable "arrows" features (and parts thereof of such "arrows") of a diamond gemstone being selectably activated for viewing in response to corresponding facets of the gemstone being selectably illuminated in accordance with the given sequence. Referring to the sequence of FIG. 5, the frames are summarised as follows:

In frame 1, all 8 LEDs of the first light source are switched OFF

In frame 2, all 8 LEDs of the first light source are switched ON

Figure 6:
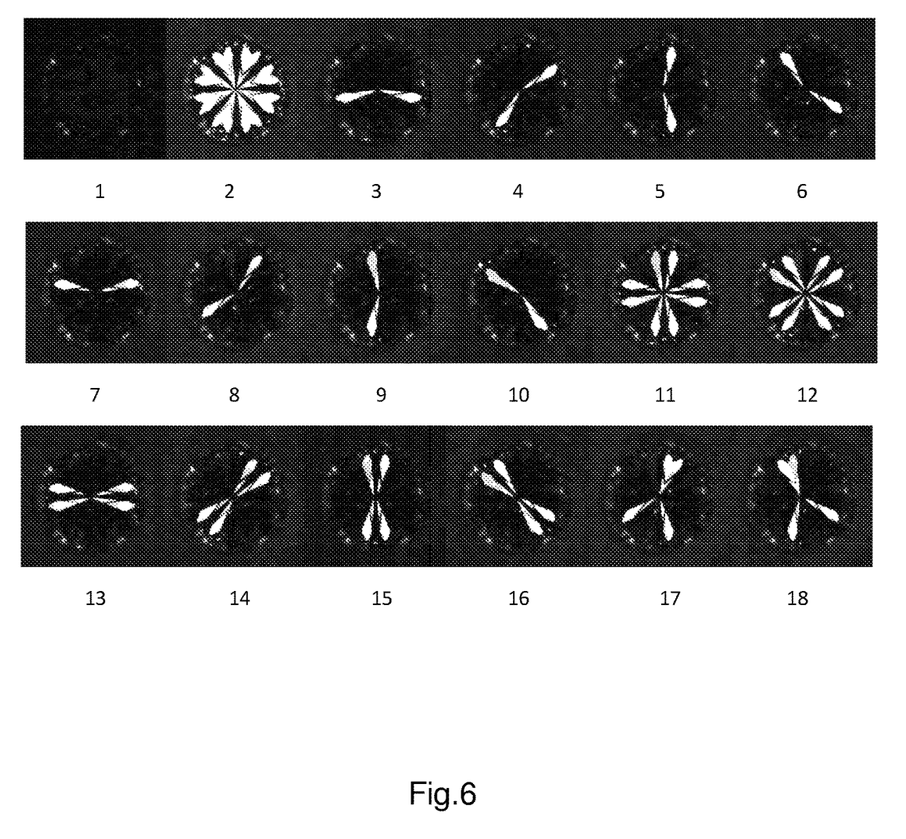
FIG. 6 shows an exemplary sequence of light-activatable features of a gemstone wherein the light-activatable features form an optically-viewable pattern including representations of "hearts" and part "hearts"
Figure 7:
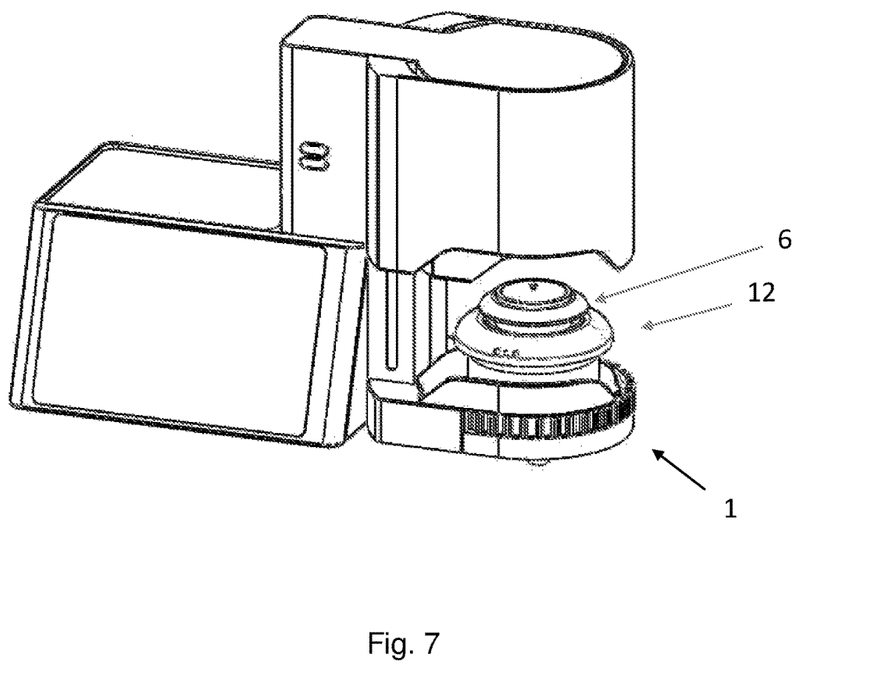
FIG. 7 shows an exemplary embodiment of the present invention in the form of a portable unit for selectably viewing at least one light-activatable feature of a plurality of light-activatable features of a gemstone.

In frame 3, LED #1 of the first light source is switched ON, all other LEDs of the first light source are switched OFF In frame 4, LED #2 of the first light source is switched ON, all other LEDs of the first light source are switched OFF In frame 5, LED #3 of the first light source is switched ON, all other LEDs of the first light source are switched OFF In frame 6, LED #4 of the first light source is switched ON, all other LEDs of the first light source are switched OFF In frame 7, LED #5 of the first light source is switched ON, all other LEDs of the first light source are switched OFF In frame 8, LED #6 of the first light source is switched ON, all other LEDs of the first light source are switched OFF In frame 9, LED #7 of the first light source is switched ON, all other LEDs of the first light source are switched OFF In frame 10, LED #8 of the first light source is switched ON, all other LEDs of the first light source are switched OFF In frame 11, LED #1, 3, 5, 7 of the first light source are switched ON, and LEDs #2, 4, 6, 8 of the first light source are switched OFF In frame 12, LED #2, 4, 6, 8 of the first light source are switched ON, and LEDs #1, 3, 5, 7 of the first light source are switched OFF In frame 13, LED #1, 5 of the first light source are switched ON, and LEDs #2, 3, 4, 6, 7, 8 of the first light source are switched OFF In frame 14, LED #2, 6 of the first light source are switched ON, and LEDs #1, 3, 4, 5, 7, 8 of the first light source are switched OFF In frame 15, LED #3, 7 of the first light source are switched ON, and LEDs #1, 2, 4, 5, 6, 8 of the first light source are switched OFF In frame 16, LED #4, 8 of the first light source are switched ON, and LEDs #1, 2, 3, 5, 6, 7 of the first light source are switched OFF In frame 17, LED #2, 3, 4 of the first light source are switched ON, and LEDs #1, 5, 6, 7, 8 of the first light source are switched OFF In frame 18, LED #6, 7, 8 of the first light source are switched ON, and LEDs #1, 2, 3, 4, 5 of the first light source are switched OFF FIG. 6 shows a further exemplary sequence (depicted by frames 1 to 18) of light-activatable "hearts" (and parts thereof of such "hearts") of a diamond gemstone being selectably activated for viewing in response to corresponding facets of the gemstone being selectably illuminated in accordance with the given sequence. Referring to the sequence of FIG. 6, the frames are summarised as follows:

In frame 1, all 8 LEDs of the first light source are switched OFF

In frame 2, all 8 LEDs of the first light source are switched ON

In frame 3, LED #1 of the first light source is switched ON, all other LEDs of the first light source are switched OFF In frame 4, LED #2 of the first light source is switched ON, all other LEDs of the first light source are switched OFF In frame 5, LED #3 of the first light source is switched ON, all other LEDs of the first light source are switched OFF In frame 6, LED #4 of the first light source is switched ON, all other LEDs of the first light source are switched OFF In frame 7, LED #5 of the first light source is switched ON, all other LEDs of the first light source are switched OFF In frame 8, LED #6 of the first light source is switched ON, all other LEDs of the first light source are switched OFF In frame 9, LED #7 of the first light source is switched ON, all other LEDs of the first light source are switched OFF In frame 10, LED #8 of the first light source is switched ON, all other LEDs of the first light source are switched OFF In frame 11, LED #1, 3, 5, 7 of the first light source are switched ON, and LEDs #2, 4, 6, 8 of the first light source are switched OFF In frame 12, LED #2, 4, 6, 8 of the first light source are switched ON, and LEDs #1, 3, 5, 7 of the first light source are switched OFF In frame 13, LED #1, 5 of the first light source are switched ON, and LEDs #2, 3, 4, 6, 7, 8 of the first light source are switched OFF In frame 14, LED #2, 6 of the first light source are switched ON, and LEDs #1, 3, 4, 5, 7, 8 of the first light source are switched OFF In frame 15, LED #3, 7 of the first light source are switched ON, and LEDs #1, 2, 4, 5, 6, 8 of the first light source are switched OFF In frame 16, LED #4, 8 of the first light source are switched ON, and LEDs #1, 2, 3, 5, 6, 7 of the first light source are switched OFF In frame 17, LED #3 and 6 of the first light source are switched ON, and LEDs #1, 2, 4, 5, 7, 8 of the first light source are switched OFF In frame 18, LED #4 and 7 of the first light source are switched ON, and LEDs #1, 2, 3, 5, 6, and 8 of the first light source are switched OFF Whilst it is possible for the illumination of the hearts and arrows features on the diamond to be discretely activated in nature—that is, either discretely "switched on" or "switched off", in certain embodiments it is also possible for the illumination of the hearts and arrows light-activatable features to be of variably activated for instance by varying the intensity of illumination of the first light source LEDs incident upon corresponding portions of the gemstone to selectably activate the features along a sliding-scale of intensities.

As shown in the exemplary lighting sequences of FIGS. 5 and 6, to selectably activate all 8 light-activatable arrows features and all 8 light-activatable hearts features at once, all 8 of the LEDs of the first light source are switched on simultaneously and illuminating the corresponding portions of the gemstone required to result in light-activation of the features. Conversely, to switch off all 8 hearts and arrows at any given time, all 8 LEDs of the first light source are switched off simultaneously. As there are 8 hearts and 8 arrows that may be selectably activated for viewing on the "hearts and arrows" cut diamond, a total of 256 different illuminated light-activatable hearts patterns and 256 light-activatable patterns features may be viewable. Different numbers of optically-viewable patterns comprising light-activatable features may be capable of generation in accordance with predetermined sequencing on different types of gemstones having different types of cuts.

A second light source (3) comprising a plurality of coloured LEDs such as red and blue LEDs are operably mounted on the outer ring of the PCB (5) in an even distribution around the periphery of the outer ring. In these embodiments the coloured LEDs are configured to illuminate the gemstone at any given time to provide a specific background colour which is perceived to create an appropriate atmosphere matching the theme of the pattern being viewed. In the embodiments individual LED bulbs are bent so that light emitted from the coloured LEDs point towards the light diffusor (9) which assists in transforming the coloured light emissions from being point sources in to relatively softly spreading and evenly distributed coloured light source emissions. By way of example in FIG. 4, a blue coloured background (16) is shown complementing the pattern of light-activated star feature (17) pattern that is optically-viewable.

A third light source (4) comprising a plurality of white LEDs are also operably mounted on the outer ring of the PCB (5) in an even distribution around the periphery of the outer ring. All 8 white light LEDs are switched on and the gemstone is rotated on the fixture assembly (12) to produce a viewable sparkling effect. A sparkling effect may be produced using other suitable arrangements and techniques in alternative embodiments so as to complement the aesthetics of the sequence of light-activatable features that are optically-viewable.

As will be understood, relative rotational movement between the gemstone and the third light source, will provide a more gradual illumination of portions of a gemstone, and thus may provide a more natural sparkling effect. This may be in combination with sequential activation of the LEDs. Those skilled in the art will appreciate that the light source may be rotated and the gemstone remained fixed, or vice versa.

Those skilled in the art will also appreciate that whilst all three light sources are shown as being on the same PCB (5) and at the same altitude from the gemstone, in other or alternate embodiments the light sources may be separate and at different altitudes. For example, the third light source could be located closer to the gemstone or below the gemstone, and appropriate reflector and/or different coloured light may be utilized within different embodiments without departing from the invention.

The optical magnifying unit (10) in these embodiments includes a dual-camera microscope with an objective lens extending downwardly towards the diamond to be viewed. The microscope system consists of 2 optical paths with different magnification ratios. The light after passing through the objective lens is split by a semi-transparent mirror. A certain amount of light is transmitted along the overview path which has a magnification ratio of 0.3×. The camera in this path captures a wide-ranged view that covers the whole gemstone up to around the size of a 5 carat circular-shaped diamond. The remaining amount of light is transmitted along the marking view path which has a magnification ratio of 4.5×. The camera in this path captures a zoomed-in view that covers only around 3 times the height of a mark on gemstone. This magnification ratio also covers common marks such as GIA mark on the girdle of a diamond.

An advantage of dual camera system is that once an object is in focus, there is no need to re-focus again when the user toggles between overview and marking view. The user can choose to display only the overview or marking view, or one view as major screen and another as minor screen overlapped on it. The positions of the two CCDs are adjusted to meet the following requirements:
  (i) Once the marking view is in-focus, the overview is also in-focus.
  (ii) The centre of the overview is aligned to the centre of the marking view.
  (iii) The centre of the coaxial light spot is aligned to both centres of the overview and the marking view.

The CCD centres after tuning are defined as the axis of optical system. This allows the user to make use of the overview to search for the mark in the marking view. For example, if mark is engraved at the centre on the table surface of a gemstone, the user can roughly locate the mark in the marking view by simply aligning the gemstone centre to the centre of the overview.

A movable cover is designed to embrace the focus point. It is actuated by electric motor and its up and down motions are controlled by two buttons on the viewer casing.

When the cover is opened, the user is allowed to put and take out the gemstone under the optics in the viewer and adjust the holding fixture for clear display of the mark.

When the cover is closed, it has two functions,
  (i) Protect the user by blocking the laser from going out from the viewer.
  (ii) Eliminate the disturbance of ambient lighting.

Users can use the overview for the following purposes:
  (i) Aligning any point on a gemstone to the optical centre for viewing by the marking view.
  (ii) Adjusting the tilting angle of the gemstone surface. If the tilting angle of the gemstone table is perpendicular to the optical axis, the whole coaxial light spot with its centre aligned with the optical centre is reflected from the gemstone table surface.
  (iii) These two functions in turn assist the operator to find the mark on the gemstone in the marking view.
  (iv) Displaying of the shape and cutting of a gemstone.
  (v) Displaying of specific pattern of a gemstone. For example, the 8-arrows pattern and 8-hearts pattern of a diamond.
  (vi) Displaying of sparkling effect of a gemstone.

Figure 3:
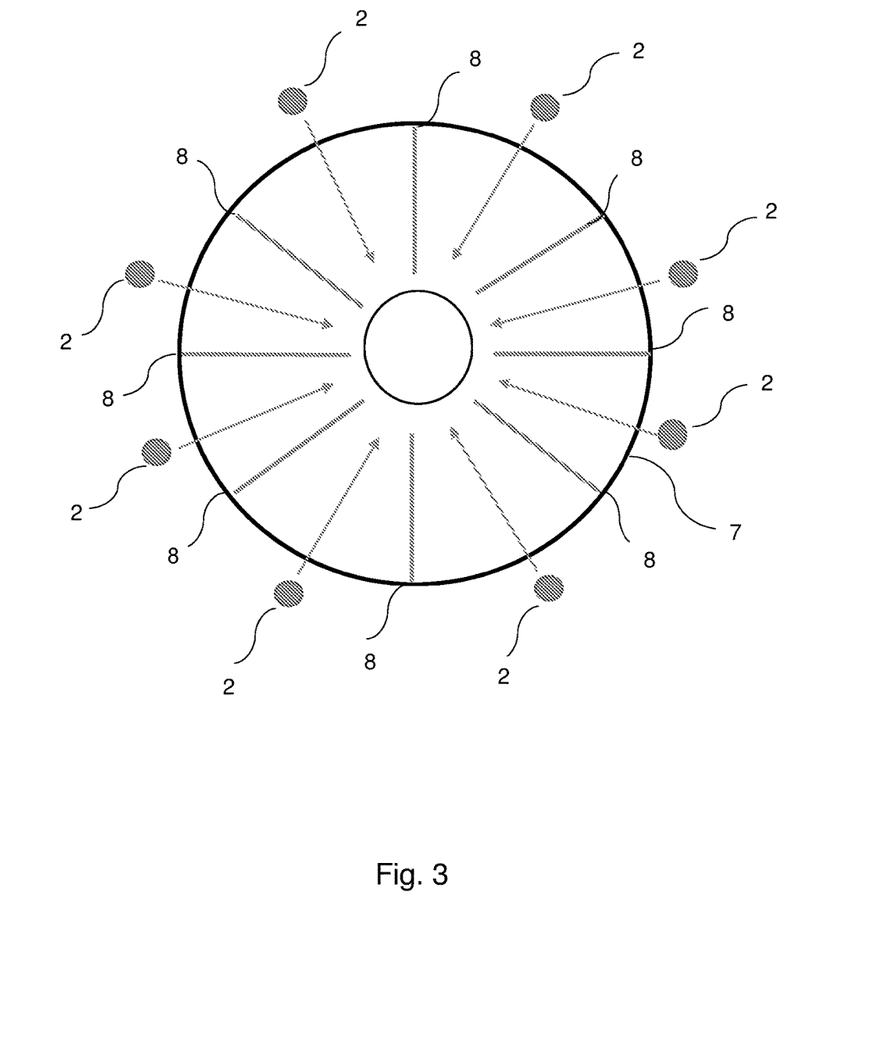
FIG. 3 shows a bottom view of the conical reflector with LED separators for separating light from each of the LEDs, in accordance with an embodiment of the present invention.

Users can use the marking view for the following purposes:
  (i) Viewing the mark on the table surface of a gemstone (either lighted up by coaxial light or laser, or both at the same time)
  (ii) Viewing the mark on the girdle of a gemstone The concentric rings of the PCB (5) are positioned so as to surround the objective lens of the microscope. The conical reflector has a center-opening shaped and dimensioned to allow coaxially emitted light from within the optics of the microscope to pass therethrough, and, for light reflected from the diamond being illuminated to return back through for the viewing by the microscope. This provides for lighting that is substantially parallel to the optical axis of the microscope. The aperture on the light source controls the spot size of the coaxial light projected on the focus plane of the microscope.

The inner surface of the conical reflector is black in colour for minimal reflection of light during viewing by the microscope. The outer surface of the conical reflector is white in colour so that the light emitted by the 8 LEDs of the first light source (2) on the inner ring are reflected maximally towards the object. The angle of the cone is designed so that, corresponding to the specific working distance of the microscope system, the light emitted by each of the 8 LEDs is reflected towards the focusing point of the microscope with specific incoming angle. The dimension of the conical reflector provides a lighting angle from around 75 degrees to around 83 degrees. This angle meets the requirement for displaying the 8-arrows or 8-hearts pattern of a diamond. Also, to assist in directing light from each of the 8 LEDs of the first light source (2) towards the diamond to selectably illuminate the corresponding portions of the diamond required to selectably activate light-activatable features such as hearts or arrows of the diamond, the LEDs are bent so that they are pointing inward horizontally towards the outer surface of the conical reflector.

The outer surface of the conical reflector (7) includes a separator (8) structure which separates the conical reflector into 8 evenly distributed regions bounded by a partition wall on each side. Light emitted by a specific LED is incident upon only its respective region of the reflector between the partition walls and in turn the light incident upon the respective region of the reflector is reflected from the reflector on the diamond to light up a particular feature of the diamond. The separator is black in colour to reduce any reflection of light by it.

Embodiments of the present invention also include an electronic system configured to provide the following functionality:
  a touchscreen for display of a user interface, input adjustment, and operating option selections;
  an operating system board—for running of user interface and executing application program, including systems such as an Android operating system
  a microcontroller unit (MCU) (15)—for connection to power and reset switches, USB port, power source, light source, UHF module and Wi-Fi module, etc;
  an Ultra High Frequency (UHF) module configured for sensing the RFID tag on the individual package of gemstones for collecting information such as size of that particular gemstone;
  a Wi-Fi communication module configured for connecting embodiments of the present invention to the Internet and online databases, and, for transferring videos, images, animations and other data captured by the viewer to a portable displaying device such as a smartphone which may be operated by a customer or other user.

Regarding the MCU (15) it is further configured for operably interfacing with the first (2), second (3) and third (4) light sources so as to cause the light sources to illuminate the facets of the gemstone (6) corresponding to light-activatable features of the gemstone in accordance with a predetermined sequence of illumination patterns on the visual display unit which for instance can be a television display disposed on the system (1), or, a smartphone display screen via a wireless communication link such as that based on Wi-Fi, UHF, NFC, Bluetooth or any other suitably configured wireless technology. The display of the predetermined sequence of illumination patterns is configured for synchronisation with a musical track so as to visually complement the musical track.

The present invention provides distinct advantages over those of the prior art, by providing a method, system and device that provides for selectably viewing at least one light-activatable feature of a plurality of light-activatable features of a gemstone. Such a method, system and device provides for:

(1) Individual lighting of a light-activatable feature,
(2) as well as control of which feature is activated, and when it is activated.

As is known by those skilled in the art, cutting is known to maximise the return of all available light applied to a diamond, which is a result of all of the facets being in precise alignment with each other. This affects the value of diamonds of such grade of cut, such as "Hearts and Arrows" cut.

Also, as known by those skilled in the art, the "Hearts and Arrows" phenomena vary with cut precision, and whilst a diamond may exhibit this pattern, imperfections include:

Hearts are inconsistent with varied separation from V's uneven separation between heart tips and the V's, Hearts being similar, but are not well shaped and beginning to separate Crooked hearts and asymmetrical appearance makes this pattern unacceptable.

Arrows are distorted by "flagging, side effects and clustering" and are unacceptable.

Side effects distort the arrows and make the pattern weak.

Crooked and asymmetrical arrows, triangles are also scattered showing weak symmetry.

Arrows are asymmetrical and do not "light-up" evenly, due to steep and varied angles of the crown and pavilion.

The present in invention utilizes the concept of Individual lighting of a light-activatable feature, and control of which feature is activated, for applications:

(i) Demonstrating the quality of the cut precision of a gemstone
(ii) Assistance in grading and rating of gemstones
(iii) Identification of gemstones, including the aspects of:
Assessing authenticity
Gemstone identification
Demonstrating origin
Security identification
Anti-counterfeiting Whilst the patterns viewed of such gemstones using techniques and equipment allows for the viewing and assessment of a pattern, the whole pattern is displayed at the same time.

This does not allow for viewing or assessment of individual features which comprise the pattern, due to facet reflections which overlap with each other forming the pattern.

As such, optical assessment of patterns may mask disparities between individual features which form the pattern, thus preventing individual assessment, when viewing the whole pattern as in the prior art when all light activatable features are simultaneously activated.

The present invention, by providing individual features of a pattern to be viewed as opposed to the prior art, provides for:

(a) increased optical assessment of cut precision
(b) optical characterization of individual features of a pattern Accordingly, the present invention may be used as follows.

Sales Environment

Gemstones, such as precision cuts of Hearts and Arrows, are often marketed by demonstration of the symmetry and quality of a pattern, to customers. Such demonstrations are indicative of the quality of the cut symmetry to customers, who may view such diamonds using existing viewing devices which display the pattern.

The present invention allows for individual features to be demonstrated individual features of the pattern, for greater visual indication of the precision of a diamond, and allowing enhanced examination, without interference from reflections forming other features of the pattern.

Further, the controllability of the activation of such individual features, provides the ability to provide predetermined feature or multiple feature display routines, Thus, individual optically viewable features of the pattern and control thereof, is beneficial for commercial purposes and in support of asserted cut quality. This may be performed in wholesale or point of sale for example. At point of sale, a customer may readily see that a diamond has cut parameters which cause a particular pattern, including individual feature examination.

Grading

The present invention provides a non-contact method for increased parametisation of facet orientation and precision, by allowing individual features of a pattern to be characterized and mapped against a standard, and provide rating regimes.

The present invention allows for cut parameters to be assessed without the necessity of complex three-dimensional measuring equipment, and allows the grade of a gemstone to be readily demonstrated to customers in point of sale environment.

Identification

By providing increased gemstone cut characterisation, the present invention allows multiple cut parameters of a gemstone to be assessed, providing a unique dataset to be formed in respect of an individual gemstone.

As such, a gemstone may be identified without the use of marking being provided to the surface of a gemstone.

Industrial and commercial applications include assessing authenticity, gemstone identification, demonstrating origin, security identification and anti-counterfeiting measures.

In embodiments of the invention, optically acquired data may be captured, and datasets generated therefrom.

In other embodiments, devices and systems of the present invention may provide for the viewing of markings on a facet of a gemstone.

Accordingly, the system may further include a coaxial light as further light source other than the first, second or thirds light sources mounted on the PCB. The coaxial light source may be emitted from within the optical acquisition device, and it is used for the viewing of markings such as protruded mark and engraved mark, other marks such as Forever mark, GIA mark and the like.

Additional light sources may be provided, for the viewing of certain marks when the mark is non-optically detectable in the visible light spectrum.

Protruded Marking

Such a marking may be provided by one or more protrusions formed on an outer surface of a polished facet of the gemstone, wherein the polished facet of the solid state material has an average surface roughness of less than 50 nm.

A gemstone may have a plurality of protrusions formed which are nanometer sized so as so provide an information mark invisible to the naked eye due to Rayleigh Criterion in optical limit, and said one or more protrusions are arranged in a periodic array viewable by specified lighting conditions and by a camera equipped microscope in the visible and invisible light range.

In an embodiment one or more protrusions are adjoined to an adjacent protrusion, so as to form a continuous nano-protrusion marking arranged in a periodic array viewable by specified lighting conditions and by a camera equipped microscope in the visible and invisible light range.

A system or device according to the present invention may further including a further light source for illuminating said marking for detection and viewing of the marking by an optical magnifying unit, wherein upon application of specific lighting conditions or the optical viewing conditions the optical viewing unit may view the marking in the visible and invisible light range.

Such a marking on the gemstone is formed by a method including the step of applying focused inert gas ion beam local irradiation towards an outer surface of a polished facet of the gemstone in a way of protruding top surface material; wherein irradiated focused inert gas ions from said focused inert gas ion beam penetrate the outer surface of said polished facet of said gemstone; and irradiated focused inert gas ions cause expansive strain within the solid state crystal lattice of the gemstone below said outer surface at a pressure so as to induce expansion of solid state crystal lattice, and form a protrusion on the outer surface of the polished facet of the gemstone. The focused inert gas ion beam has a beam energy in the range of from 5 keV to 50 keV and probe current 1 fA to 200 pA, and the solid state crystal lattice is in a form of single crystalline, poly-crystalline, or amorphous form.

Irregular Entity Marking

A system or device of the present invention may provide for reading of a further identifiable mark on an article on a portion of a polished facet of a surface of a gemstone, and may further comprise:
- a light source for incident light having one or more predetermined wavelengths at a predetermined angle of incidence to the identifiable mark; and
- an optical viewing device for viewing said identifiable mark at said requisite viewing angle by way of an optical viewing device such that a local maxima is detected,
- wherein the identifiable mark comprises a nano-structure formed by a two-dimensional or a three-dimensional lattice of a plurality of discrete nanometer sized recessed or protruded entities, wherein said entities are arranged within a predefined region of said polished facet in a predetermined arrangement in relation to each other, and such that an outer interface surface between the facet of the article and air is formed and an inner interface surface between the facet of the article and air is formed;
- wherein said predetermined arrangement of said entities is a non-uniform and non-periodic arrangement, and wherein said entities are sized and shaped so as to cause optical scattering upon reflection of incident light, and the distance from the inner interface surface to the outer interface surface is greater than the amplitude of the non-marked portion of said polished facet;
- such that upon reflection of incident light having one or more predetermined wavelengths by said lattice at a predetermined angle of incidence to said lattice, interference due to scattering of light from said lattice is induced, such that reflected light has a variation in intensity providing one or more local maxima of one or more wavelengths; and
- said mark is identifiable by way of the optical viewing device inclined at a requisite viewing angle such that a local maxima is detected.

The non-optically detectable identifiable mark is non-optically detectable in the visible light spectrum is viewable in the ultra-violet (UV) spectrum, and the system includes an ultra-violet light source for illuminating said marking.

The system or device may further include Differential Interference Contrast (DIC) microscope or Scanning Electron Microscopy (SEM) for viewing of said marking.

Such marks are optically invisible, and a red laser maybe included within the system, in order to activate such a marking and make it viewable Other Marking Other marks which may be detected by a system or apparatus may be formed by a method including the steps of:
(i) forming a plurality of recesses within a predetermined region of a photoresist applied to an outer surface of an article formed from a solid state material, wherein said plurality of recesses is formed by two-photon absorption lithography and wherein said one or more recesses extend at least partially through the photoresist and from an outer surface of the photoresist and towards said outer surface of the article formed from a solid state material; and
(ii) applying an etching process such that at least a portion of the outer surface of said article is exposed and etched so as to form a plurality of etched portions extending into said article from the outer surface of the article and corresponding to said plurality of recesses;
wherein said predetermined region of said photoresist defines an identifiable mark to be applied to the outer surface of said article; wherein said plurality of etched portions forms the non-optically identifiable mark on the outer surface of said article; and wherein the maximum width of the etched portions is less than 200 nm such that the identifiable mark is non-optically detectable in the visible light spectrum.

Those skilled in the art will appreciate that the invention described herein is susceptible to variations and modifications other than those specifically described without departing from the scope of the invention. All such variations and modification which become apparent to persons skilled in the art, should be considered to fall within the spirit and scope of the invention as broadly hereinbefore described. It is to be understood that the invention includes all such variations and modifications. The invention also includes all of the steps and features, referred or indicated in the specification, individually or collectively, and any and all combinations of any two or more of said steps or features.

The reference to any prior art in this specification is not, and should not be taken as, an acknowledgment or any form of suggestion that that prior art forms part of the common general knowledge.

What is claimed is:

1. A method of selectably viewing at least one light-activatable feature of a plurality of light-activatable features, said light-activatable feature being formed from reflection of light from facets of a gemstone and being viewable from the crown pavilion of said gemstone, wherein at least one portion of a plurality of portions of the gemstone corresponding to the at least one light-activatable feature is selectably illuminated by a first light source so as to selectably activate said at least one light-activatable feature and to provide said selectable viewing thereof and wherein the plurality of light-activatable features of the gemstone form an optically viewable pattern.

2. A method as claimed in claim 1, wherein the plurality of light-activatable features of the gemstone form an optically-viewable pattern, and wherein the optically-viewable pattern includes at least one of a plurality of hearts, a plurality of arrows, a star and a plurality of triangles, and wherein facet reflections which overlap with each other form said optically viewable pattern.

3. A method as claimed in claim 1 wherein the plurality of portions of the gemstone include facets of the gemstone.

4. A method as claimed in claim 1 further including illuminating the gemstone so as to produce a viewable coloured background feature of the gemstone by way of a second light source.

5. A method as claimed in claim 1 further including illuminating the gemstone so as to produce a viewable sparkling feature of the gemstone by way of a third light source, wherein the third light source includes a plurality of white light LEDs.

6. A system for selectably viewing at least one light-activatable feature of a plurality of light-activatable features, said light-activatable feature being formed from reflection of light from facets of a gemstone and being viewable from the crown or pavilion of said gemstone, the system including:
a first light source configured for selectably illuminating at least one portion of a plurality of portions of the gemstone corresponding to the at least one light-activatable feature of the gemstone wherein the at least one light-activatable feature of the gemstone is activated in response to selectable illumination of the at least one portion of the gemstone;
an optical acquisition device configured for optically acquiring an optically viewable representation of the at least one light-activated feature which is activated in response to selectable illumination of the at least one corresponding portion of the gemstone; and wherein the plurality of light-activatable features of the gemstone form an optically-viewable pattern.

7. A system in claim 6, wherein the plurality of portions of the gemstone include facets of the gemstone.

8. A system as claimed in claim 6 wherein the first light source includes an infrared light source and/or wherein the first light source includes an LED light source.

9. A system as claimed in claim 6 wherein the first light source includes a plurality of LEDs.

10. A system as claimed in claim 6 wherein the at least one light-activatable feature of the gemstone is able to be selectably activated discretely or variably.

11. A system as claimed in claim 6, further including a light separator configured for directing light emitted from the first light source to selectably illuminate the at least one portion of the gemstone corresponding to the light-activatable feature so as to activate the at least one light-activatable feature.

12. A system as claimed in claim 6 further including a second light source configured for illuminating the gemstone so as to produce a viewable coloured background feature of the gemstone.

13. A system as claimed in claim 12 wherein the second light source includes at least one of a red coloured light source and a blue coloured light source and/or wherein the second light source includes a plurality of coloured light LEDs.

14. A system as claimed in claim 13, further including a diffusor configured for diffusing light emitted from the second light source.

15. A system as claimed in claim 6, further including a third light source configured for illuminating the gemstone so as to produce a viewable sparkling feature of the gemstone,
wherein the third light source includes a plurality of white light LEDs,
wherein the system further comprises a rotation assembly for rotation of one of the light sources and the gemstone relative to each other about the viewing axis of the optical acquisition device, such that light from said of the light sources is applied towards the gemstone from one facet to an adjacent facet upon said rotation; and, wherein the rotation assembly provides rotation of the third light source and the gemstone relative to each other, and
wherein light applied towards the gemstone is applied with a constant intensity from a facet of the gemstone to an adjacent facet throughout rotation so as to provide said viewable sparkling feature of the gemstone.

16. A system as claimed in claim 6, further including an optical viewing unit for viewing the optical representation of the light-activatable feature of the gemstone optically acquired by the optical acquisition device wherein the optical viewing unit includes at least one of a television display, a computer monitor, and a display screen of a smartphone or portable communication device.

17. A system as claimed claim 6, further including a magnifying unit for optically magnifying the representation of the light-activatable feature of the gemstone, and
wherein the magnification unit is configured to provide a first magnified view comprising a relatively lower magnification of the representation of the light-activatable feature of the gemstone and a second magnified view comprising a relatively higher magnification of a representation of another feature of the gemstone, wherein said another feature of the gemstone includes a marking feature, and wherein the optical viewing unit is configured to display the first and second magnified views interchangeably, or, concurrently whereby the first magnified view is displayed inset within the second magnified view.

18. A system as claimed in claim 6, further including a controller for controlling at least one of the first light source, to illuminate the gemstone in accordance with a predetermined lighting sequence.

19. A system as claimed in claim 18, further including a device for synchronising the predetermined lighting sequence to music.

20. A system as claimed in claim 6 wherein the first light source is configured to illuminate the at least one portion of the plurality of portions of the gemstone at an angle approximately in a range of about 75 to 83 degrees.

21. A system according to claim 6, further comprising a processor for comparing said optically viewable representation of the at least one light-activated feature with known optical representations, whereby said known optical representations are indicative of a particular gemstone; whereby the system provides for verifying the identity of a gemstone; and wherein the plurality of light-activatable features of the gemstone form an optically-viewable pattern, and wherein facet reflections which overlap with each other form said optically viewable pattern.

22. A system according to claim 6 further comprising a processor for comparing said optically viewable representation of the at least one light-activated feature known optical representations, whereby said known optical representations are indicative of a cut parameter of the facets of the gemstone, whereby the system provides for assessing the precision of a plurality of cuts of a gemstone.

23. A method of verifying the identity of a gemstone, said method comprising:
  selectably illuminating at least one portion of a plurality of portions of a gemstone corresponding to at least one light-activatable feature, said light-activatable feature being formed from reflection of light from facets of a gemstone and being viewable from the crown or pavilion of the gemstone wherein the at least one light-activatable feature of the gemstone is activated in response to selectable illumination of the at least one portion of the gemstone;
  acquiring an optically viewable representation of the at least one light-activated feature which is activated in response to selectable illumination of the at least one corresponding portion of the gemstone; and
  comparing said optically viewable representation with a known optical representation, whereby said known optical representations are indicative of a particular gemstone.

* * * * *